(12) United States Patent
Kumar et al.

(10) Patent No.: US 10,022,560 B2
(45) Date of Patent: Jul. 17, 2018

(54) AUTOMATION OF THERAPY PLANNING

(71) Applicant: KONINKLIJKE PHILIPS N.V., Eindhoven (NL)

(72) Inventors: Prashant Kumar, Bangalore (IN); Karl Antonin Bzdusek, Madison, WI (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 198 days.

(21) Appl. No.: 14/908,226

(22) PCT Filed: Jul. 11, 2014

(86) PCT No.: PCT/IB2014/063020
§ 371 (c)(1),
(2) Date: Jan. 28, 2016

(87) PCT Pub. No.: WO2015/015343
PCT Pub. Date: Feb. 5, 2015

(65) Prior Publication Data
US 2016/0166855 A1 Jun. 16, 2016

Related U.S. Application Data

(60) Provisional application No. 61/860,415, filed on Jul. 31, 2013.

(51) Int. Cl.
*A61N 5/10* (2006.01)

(52) U.S. Cl.
CPC .......... *A61N 5/1039* (2013.01); *A61N 5/1038* (2013.01)

(58) Field of Classification Search
CPC ...................... A61N 5/1038; A61N 5/1039
See application file for complete search history.

(56) References Cited

U.S. PATENT DOCUMENTS 6,546,073 B1 4/2003 Lee et al.
6,754,374 B1 6/2004 Miller et al.
(Continued)

FOREIGN PATENT DOCUMENTS

DE 102010004384 7/2011
WO 2008/120116 10/2008
(Continued)

OTHER PUBLICATIONS

Bzdusek K, Friberger H, Eriksson K, et al. Development and evaluation of an efficient approach to volumetric arc therapy planning. Med Phys 2009; 36: 2328-39.
(Continued)

*Primary Examiner* — Christine H Matthews
*Assistant Examiner* — Joshua D Lannu

(57) ABSTRACT

An automated treatment planning system having a planning image memory which stores a volume diagnostic image; a user interface device configured for a user to input data defining a plurality of regions of interest within the volume diagnostic image; and one or more processors. The processors are configured to receive the volume diagnostic image and plurality of user-defined regions of interest indicated within the volume diagnostic image; map the plurality of regions of interest to the body atlas to determine anatomical locations within the plurality of regions of interest; map each region of interest of the plurality of regions of interest to the body atlas to select correct corresponding anatomical structures; receive a treatment plan template based upon the anatomical structures from a knowledge base. A planning module is configured to generate a treatment plan using the treatment plan template.

15 Claims, 2 Drawing Sheets

(56) References Cited

U.S. PATENT DOCUMENTS

| | | | |
|---|---|---|---|
| 7,046,762 | B2 | 5/2006 | Lee et al. |
| 7,529,339 | B2 | 5/2009 | Goldman et al. |
| 8,073,104 | B2 | 12/2011 | Yan et al. |
| 8,472,683 | B2 | 6/2013 | Manjeshwar |
| 8,577,115 | B2 | 11/2013 | Gering |
| 2009/0234175 | A1* | 9/2009 | Maier .................. A61N 5/1031 600/3 |

FOREIGN PATENT DOCUMENTS

| | | | |
|---|---|---|---|
| WO | 2009/109874 | 9/2009 | |
| WO | WO 2009109874 A1 * | 9/2009 | ............. A61B 5/055 |
| WO | 2012/012768 | 1/2012 | |
| WO | WO 2012012768 A1 * | 1/2012 | ........... A61B 6/5211 |
| WO | 2012/035463 | 3/2012 | |

OTHER PUBLICATIONS

Otto K., "Volumetric modulated arc therapy: IMRT in a single gantry arc", Med Phys 2008; 35:310-7.

Yu CX. 1995 Intensity-modulated arc therapy with dynamic multileaf collimation: an alternative to tomotherapy. Phys Med Biol 1995; 40: 1435-49.

Yu CX, Li XA, Ma LJ, et al. Clinical implementation of intensity-modulated arc therapy. Int J Radiat Oncol Biol Phys 2002; 53: 453-63.

Rosen I, Liu HH, Childress N, et al. Interactively exploring optimized treatment plans. Int J Radiat Oncol Biol Phys 2005; 61: 570-82.

Gopal R, Starkschall G. Plan space: Representation of treatment plans in multidimensional space. Int J Radiat Oncol Biol Phys 2002; 53: 1328-36.

Zhang X, Wang X, Dong L, et al. A sensitivity-guided algorithm for automated determination of IMRT objective function parameters. Med Phys 2006; 33: 2935-44.

Zhang HH, D'Souza WD, Shi L, et al. Modeling plan-related clinical complications using machine learning tools in a Multiplan IMRT framework. Int J Radiat Oncol Biol Phys 2009; 74: 1617-26.

Wu B, Ricchelli F, Sanguineti G, et al. Data-driven approach to generating achievable dose-volume histogram objectives in intensity modulated radiation therapy treatment planning. Int J Radiat Oncol Biol Phys 2011; 79: 1241-7.

Craft DL, Hong TS, Shih HA, et al. Improved planning time and plan quality through multicriteria optimization for intensity-modulated radiotherapy. Int J Radiat Oncol Biol Phys 2011.

Chung HT, Lee B, Park E, et al. Can all centers plan intensity-modulated radiotherapy (IMRT) effectively? An external audit of dosimetric comparisons between three-dimensional conformal radiotherapy and IMRT for adjuvant chemoradiation for gastric cancer. Int J Radiat Oncol Biol Phys 2008; 71: 1167-74.

Wu B, Ricchelli F, Sanguineti G, et al. Patient geometry-driven information retrieval for IMRT treatment plan quality control. Med Phys 2009; 36: 5497-505.

Petit S, Wu B, Kazhdan M, et al. Increased organ sparing using shape-based treatment plan optimization for intensity modulated radiation therapy of pancreatic adenocarcinoma. Radiother Oncol 2011; Article in press, online version.

Wu B, Sanguineti G, McNutt T, et al. Using overlap volume histogram and intensity modulated radiation therapy plan data to guide and automate volumetric modulated arc therapy treatment planning: a head-and-neck case study; Int J Radiat Oncol Biol Phys 2012; Article in press.

Wu B, Sanguineti G, Kazhdan M, et al, A knowledge-based and patient-geometryspecific automated IMRT treatment planning system. Submitted to Med Dos in Mar. 2011; under review.

Moore K, Brame S, Low D, Mutic, S, Quantitative Metrics for Assessing Plan Quality. Semin Radiat Oncol 2012 22:62-69.

\* cited by examiner

AUTOMATION OF THERAPY PLANNING

CROSS REFERENCE TO RELATED APPLICATIONS

This application is the U.S. National Phase application under 35 U.S.C. § 371 of International Application No. PCT/IB2014/063020, filed Jul. 11, 2014, published as WO 2015/015343 on Feb. 5, 2015, which claims the benefit of U.S. Provisional Patent Application No. 61/860,415 filed Jul. 31, 2013. These applications are hereby incorporated by reference herein.

The present application relates generally to radiation therapy. It finds particular application in conjunction with radiation therapy planning and will be described with particular reference thereto. However, it is to be understood that it also finds application in other usage scenarios and is not necessarily limited to the aforementioned application.

In radiation therapy planning, creating a patient specific treatment plan can be a time consuming and tedious task. Some of the steps are redundant and vary little from patient to patient or plan to plan. Some of these steps can be automated using macro languages or scripts, but certain aspects are difficult without tools for writing logical expressions, loops, and other common programming functionality.

In the past decade, technological advancements have provided a big leap in the field of intensity modulated radiation therapy (IMRT), intensity modulated proton therapy (IMPT) and the like, to improve dose delivery. One area that is difficult to automate in current treatment planning is intensity-modulated radiation therapy (IMRT) or volumetric-modulated arc therapy (VMAT) optimization. Recently the research interest has shifted towards methods of automating various tasks involved in plan generation, starting from beam placement to dose optimization, to assist and reduce the workload burden on the clinical user. Optimization is an iterative process where a user attempts to specify planning goals in the form of dose or biological objectives to create an ideal dose to target structures, typically a uniform dose, and minimize the dose to critical structures.

Plan evaluation is classified into three phases: 1. Physical evaluation, 2. Technical evaluation and 3. Clinical evaluation. The physical and technical aspects of a plan are generally examined by a technician after the completion of the plan. The clinical aspects of a plan are investigated by a radiation oncologist. Currently an IMRT plan is evaluated based on five categories that cover the physical, technical and clinical aspects of a plan: 1. Geometric analysis, 2. Dose distribution analysis, 3. Dose Volume Histogram (DVH) analysis, 4. Parametric analysis and 5. Deliverability analysis.

The geometric analysis is performed to evaluate the optimality of beams placement. Beam placement is a very important step. The quality of optimization is mainly influenced by the number of beams and their angles. Rules have been formulated for optimal beam placement in IMRT in view of increasing the optimality and deliverability of an IMRT plan.

The dose distribution analysis qualitatively verifies the optimality of dose distribution in axial, coronal and sagittal planes. This analysis can be further split up into 2D analysis and 3D analysis. 2D dose distribution analysis implies the evaluation of dose distribution slice-by-slice. This type of analysis is used to evaluate the conformity of the prescribed dose with respect to the target volume in each slice. This type of analysis can also reveal the distribution of cold or hot spots in and around the target volume. Cold or hot spots are areas within the target and organs at risk that receive less or greater than the intended dose of radiation. The 3D distribution analysis is useful in determining how conformal a dose distribution is to the overall target volume with respect to a set of beam orientations.

Dose Volume Histograms (DVH) is a powerful tool for evaluating the optimality of a plan. A DVH represents a 3-dimensional dose distribution in a graphical 2-dimensional format. A DVH for target volume graphically represents the quality of the dose distribution in terms of coverage, conformity and homogeneity. The DVH curves for Organs-at-risk (OARs) represent the efficiency at which the OARs are spared in terms of mean and maximum dose.

The parametric analysis is performed to quantitatively verify the optimality of dose. The parameters used in this analysis are: (a) minimum, mean and maximum dose for target volume and OARs and (b) coverage, conformity and homogeneity indices for target volume. Apart from physical metrics for plan evaluation, pluralities of biological metrics are used in plan evaluation. These biological metrics include Equivalent Uniform Dose (EUD), Tumor Control Probability (TCP) and Normal Tissue Complication Probability (NTCP) and the like.

Deliverability analysis is performed in order to evaluate how robust the plan is in terms of dose delivery. This analysis involves the verification of parameters such as number of segments, minimum or average monitor units (MU) per segment, Minimum Segment Area (MSA), total delivery time and the like. MU is a measure of machine output of a linear accelerator in radiation therapy. The deliverability analysis reveals whether a plan is actually deliverable or not.

Various stages of plan generation have been automated with different techniques. These techniques reduce the burden on the clinical user, i.e. a radiation technician, by automating the plan generation process, such as dose objective manipulation and IMRT/VMAT optimization. However, configuration time required for these approaches is still significant and careful mapping of various regions of interest (ROIs) and associated information to the problem solving model is required. In particular, the naming convention of ROIs and correctly mapping them to the problem solving model is useful for successful plan generation. Given the complexity involved with radiation therapy treatment plan generation, it is imperative that the user wants a certain amount of manual control and review but at the same time it stops these techniques from being fully automatic. The current auto-planning and class solutions offer one time configuration of user defined techniques which are later applied to a new patient for automatically generating a treatment plan. However, the user needs to resolve discrepancies, for the new patient plan with respect to the following 1) incorrect or missing mapping of ROIs involved, 2) Beam Placement, 3) Isocenter placement, 4) DoseGrid placement.

In accordance with one embodiment, an automated treatment planning system comprising: a planning image memory (14) which stores a volume diagnostic image; a user interface device (32) configured for a user to input data defining a plurality of regions of interest within the volume diagnostic image; a ROI mapper (34) having a processor configured to: receive the volume diagnostic image and plurality of user-defined regions of interest indicated within the volume diagnostic image; map the plurality of regions of interest of the volume diagnostic image to anatomical structures using a body atlas (35); and an auto planning module

(38) configured to generate a treatment plan using the mapped plurality of regions of interest.

In accordance with one preferred method of the present application, a method for automating treatment planning, comprising: receiving (124) a volume anatomical image of a patient including a plurality of user-defined regions of interest indicated within the image volume; mapping (126) the plurality of regions of interest of the image volume to anatomical structures using a body atlas (35); and generating (138) a treatment plan using the mapped plurality of regions of interest.

In accordance with one embodiment, an automated treatment planning system comprising: a planning image memory (14) which stores a volume diagnostic image; a user interface device (32) configured for a user to input data defining a plurality of regions of interest within the volume diagnostic image; receive user defined regions of interest in an image volume; and one or more processors configured to: receive the volume diagnostic image and plurality of user-defined regions of interest indicated within the volume diagnostic image; map the plurality of regions of interest of the volume diagnostic image to anatomical structures using a body atlas (35); and generate a treatment plan using the mapped plurality of regions of interest.

One advantage is that no configuration and mapping of ROI names is required.

Another advantage is that initial constraints are automated for named ROIs.

A further advantage is that IMRT/VMAT planning complexity is reduced.

Figure 1:
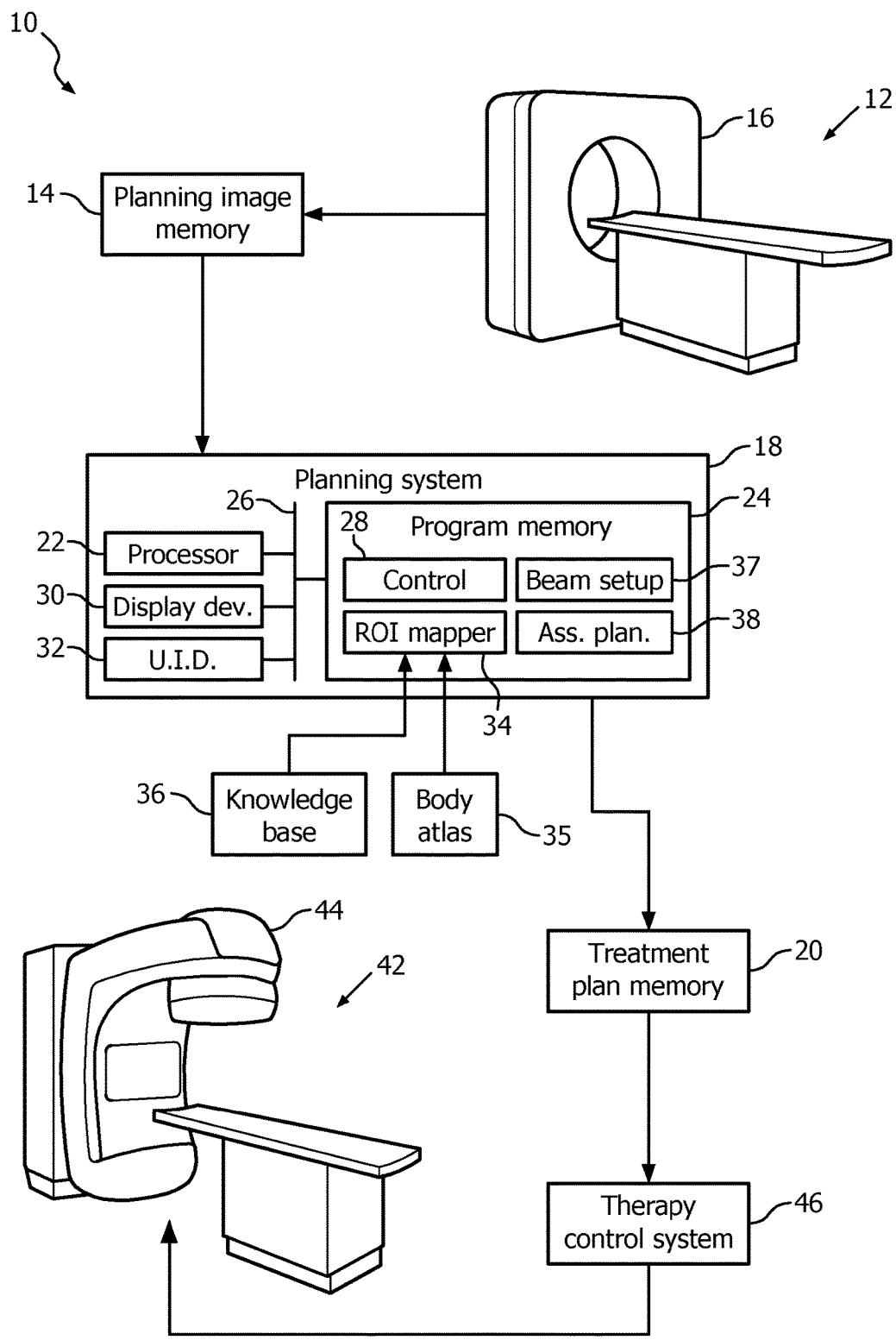
FIG. 1 depicts an IMRT planning system implementing an improved method for automating plan generation.

With reference to FIG. 1, a therapy system 10, such as an intensity-modulated radiation therapy (IMRT) system or a volumetric-modulated arc therapy (VMAT) system, includes an imaging system 12 to generate one or more planning images of a region of interest of a patient. The image volume, i.e. the planning images, is volumetric (i.e., three-dimensional) and typically stored in a planning image memory 14 of the therapy system 10. The region of interest includes one or more target structures and, typically, one or more critical structures or organs at risk (OARs). Each of the target structures is a lesion or other tissue region, such as a tumor, to be irradiated. Each of the critical structures is an organ or other tissue region which is at risk of damage from the radiation intended for the target structures, such as radiation traveling to the target structures, which has passed through the target structures, or which passes closely adjacent the target structures.

The imaging system 12 generates the planning images using one or more imaging modalities, such as computed tomography (CT), positron emission tomography (PET), magnetic resonance (MR), single photon emission computed tomography (SPECT), cone-beam computed tomography (CBCT), and the like. Hence, the imaging system 12 includes one or more scanners 16 corresponding to the imaging modalities, as well as a backend system reconstructing raw image data from the scanners into the planning images. As illustrated, the imaging system 12 generates the planning images using for example CT and includes a CT scanner 16.

A planning system 18 of the therapy system 10 generates an optimal treatment plan for the patient on the planning images, which are typically received from the planning image memory 14. The optimal treatment plan suitably includes a plurality of treatment fractions, each identifying planning target volumes (PTVs) for the target structures, margins around the target structures, dose profiles for the target structures, dose limits for the critical structures, and therapy beam directions and intensities, and is typically stored in a treatment plan memory 20 of the therapy system 10. The planning system 18 includes at least one processor 22 and at least one program memory 24. The program memory 24 includes processor executable instructions that, when executed by the processor 22, generate the optimal treatment plan. The processor 22 executes the processor executable instructions to generate the optimal treatment plan. The planning system 18 further includes at least one system bus 26 interconnecting the processor 22, the program memory 24, and any other components of the planning system 18.

A control module 28 of the processor executable instructions controls overall operation of the planning system 18, including generation of the optimal treatment plan. The control module 28 suitably displays a graphical user interface (GUI) to a user of the planning system 18 using a display device 30 of the planning system 18. Further, the control module 28 suitably allows the user to interact with the GUI using a user input device 32 of the planning system 18. For example, the user can interact with the GUI to specify parameters, controlling the generation of the optimal treatment plan. In particular, the user specifies regions of interest within the image volume located on the planning image memory 14 via the user input device 32.

A ROI mapper 34 of the processor accesses the image volume of the patient from the planning image memory 14 where regions of interest have been input by the user into the image volume. The ROI mapper 34 accesses the image volume to determine anatomical structures within the regions of interest to be irradiated. After accessing the image volume on the planning image memory 14, the ROI mapper 34 maps the input regions of interest against a body atlas 35 for determining anatomical structures within the user defined regions of interest.

The body atlas 35 is a database or other information retrieval system. The body atlas 35 is derived from information about a population of patients and is comprised of labeled anatomical structures. The body atlas 35 is used to register (rigid and/or non-rigid) the patient's image with the body atlas 35. OARs in image volume are mapped with corresponding OAR definitions from the body atlas 35, thereby providing a nomenclature of all anatomical structures within the region.

In one embodiment, the ROI mapper 34 maps the regions of interest by first mapping of the plurality of ROIs in the image volume i.e. the image mask containing all the ROIs, to the Body Atlas to determine anatomical locations. Then the ROI mapper 34 maps each individual ROI of the plurality to the Body Atlas to determine the corresponding anatomical structure. In another embodiment, when an ROI name directly matches to an atlas name, no further matching is performed.

The ROI mapper 34 determines the corresponding anatomical structure by calculating a similarity metric score, e.g. a dice score, between each ROI and every anatomical structure entry in the body atlas 35. The ROI mapper 34 ranks every anatomical structure entry in the body atlas 35 according to the similarity score and selects the anatomical structure with the highest score. If no scores are above a certain threshold no mapping may occur. The anatomical structure is then used to associate the ROI with the structure. For example, a highest similarity score is determined to be a spinal column. The region of interest is then labeled as a spinal column for use in the automated generation of the treatment plan. This is useful because the user need not follow a ROI nomenclature scheme in order to satisfy the specifics of the problem solving model. The user inputs a set of ROIs representing OARs in the image volume and the ROI mapper 34 automatically finds the right nomenclature mapping in the body atlas 35.

The ROI mapper 34 accesses a knowledgebase 36 after anatomical structures are defined within the ROIs. The knowledgebase 36 is a database or other information retrieval system. The knowledgebase 36 contains standardized clinical goals and priorities for different anatomical structures as plan templates. The plan templates are accessed through the knowledgebase 36 by the ROI mapper to create initial plan goals and priorities. The templates are then used to automatically generate a treatment plan for the patient. The clinical goals and priorities for the involved OARs are picked from the knowledgebase 36 along with the expansion margins to account for setup errors. ROIs are created for the auto-planning workflow depending on the dose level relationship of input target structures and the clinical priorities for the input OARs.

Using the knowledgebase 36, the ROI mapper 35 selects an isocenter with respect to the target anatomical structures using an automatic placement scheme at the geometrical center and further adjustment of the position to ensure that the isocenter is placed in a homogeneous tissue region instead of a cavity or high density region. Dose Grid is automatically placed to cover the input target and OARs with an additional margin, such as 1 cm.

In one embodiment, the isocenter placement is performed using an iterative approach. The isocenter is placed at the geometric center of the union ROI of all Target ROIs. Thresholding based on the CT numbers is used to identify if the isocenter is falling inside a cavity, i.e. an air region, or high density, i.e. bony, region. If it happens to fall inside a cavity or bony region, iterative adjustment of isocenter location is done until it falls in a homogeneous soft tissue region. This iterative adjustment is done only within the bounds of the union ROI and if the algorithm fails to find a suitable region, it falls back to the geometric center location.

A therapy beam setup module 37 of the processor configures one or more therapy beams used for therapy delivery. This can be performed automatically and/or manually. As to automatic therapy beam setup, an appropriate routine is employed to automatically configure parameters configuring the therapy beam. It is also contemplated that therapy beam setup can be performed using a combination of automatic and manual therapy beam setup. Beam placement is achieved using beam angle optimization methodologies along with the beam configurations followed in standard clinical practice e.g. for head and neck a standard equally spaced 7 beam co-planar configuration is enough. An additional provision to accept the number of beams input from the user is also possible, in which case the system only optimizes on the beam angles. Iterative adjustment of beam placements is also a possibility if the auto-plan results are not as desired. The automatically configured parameters can then be displayed to the user using the display device 30 and the user can modify the parameters, as appropriate, using the user input device 32. In one embodiment, with VMAT plans, automatic determination of start and stop gantry angles and couch angles are automatically determined.

Through the template of the knowledgebase 36, input parameters are picked based on input delivery constraints, these can also be iteratively tuned based on the auto-plan results. Machine specific delivery constraints specified by the user are taken into account, and for the rest of parameters the system decides on suitable settings to meet the delivery goals. The goals mostly are in terms of treatment time, minimum segment area etc.

In an exemplary direct machine parameter optimization (DMPO) embodiment, the machine parameters are Minimum Segment Area, Max No. of dynamic segments, Minimum MUs per segment vary across institutions, planners and machine capability. The parameters impact plan quality and deliverability. Better dose conformity is achieved with an increased number of segments. However, the Monitor Units and the treatment time may undesirably increase as well. Similar trade-offs exists in case of other parameters. The knowledgebase 36 applies a default "best" setting available as part of the clinical knowledgebase 36 that is specific to the automatically selected anatomical structure. In an iterative fashion these parameters are tweaked if the user defined delivery constraints are not being met. In one embodiment, the knowledgebase 36 includes a standard translation of radiation treatment oncology group (RTOG) protocols, and the user has the ability to tweak the goals and priorities within the knowledgebase 36.

Once the parameters are finalized, an auto planning module 38 generates an optimal treatment plan. The auto planning module 38 includes receiving input parameters for generation of the treatment parameter from the ROI mapper 34 through the knowledgebase 36. The input parameters include the boundaries of the structures (i.e., the target structures and, typically, the critical structures) within the planning images, which are identified using the ROI mapper 34, as well as therapy beam configuration parameters, which are determined using the therapy beam setup module 36. In one embodiment, automatically generating optimal treatment plans uses an algorithm such as the one described in U.S. Provisional Application Ser. No. 61/719,528 to Bzdusek, et al. It automatically drives the IMRT optimizer by formulating dose objectives and manipulating them iteratively. The dose objective parameters are decided based the knowledge base which defines the clinical goals and priorities.

A delivery system 42 executes the optimal treatment plan to deliver therapy, such as ablation therapy, external beam radiation therapy and/or brachytherapy, to the patient. The therapy typically includes radiation, such as one or more of x-rays, protons, high-intensity focused ultrasound (HIFU), and the like. The delivery system 42 includes a delivery apparatus 44, such as a linear particle accelerator, and a control system 44, which controls the delivery apparatus 46 in accordance with the optimal treatment plan. The optimal treatment plan is typically received from the treatment plan memory 20, but other sources are contemplated.

Figure 2:
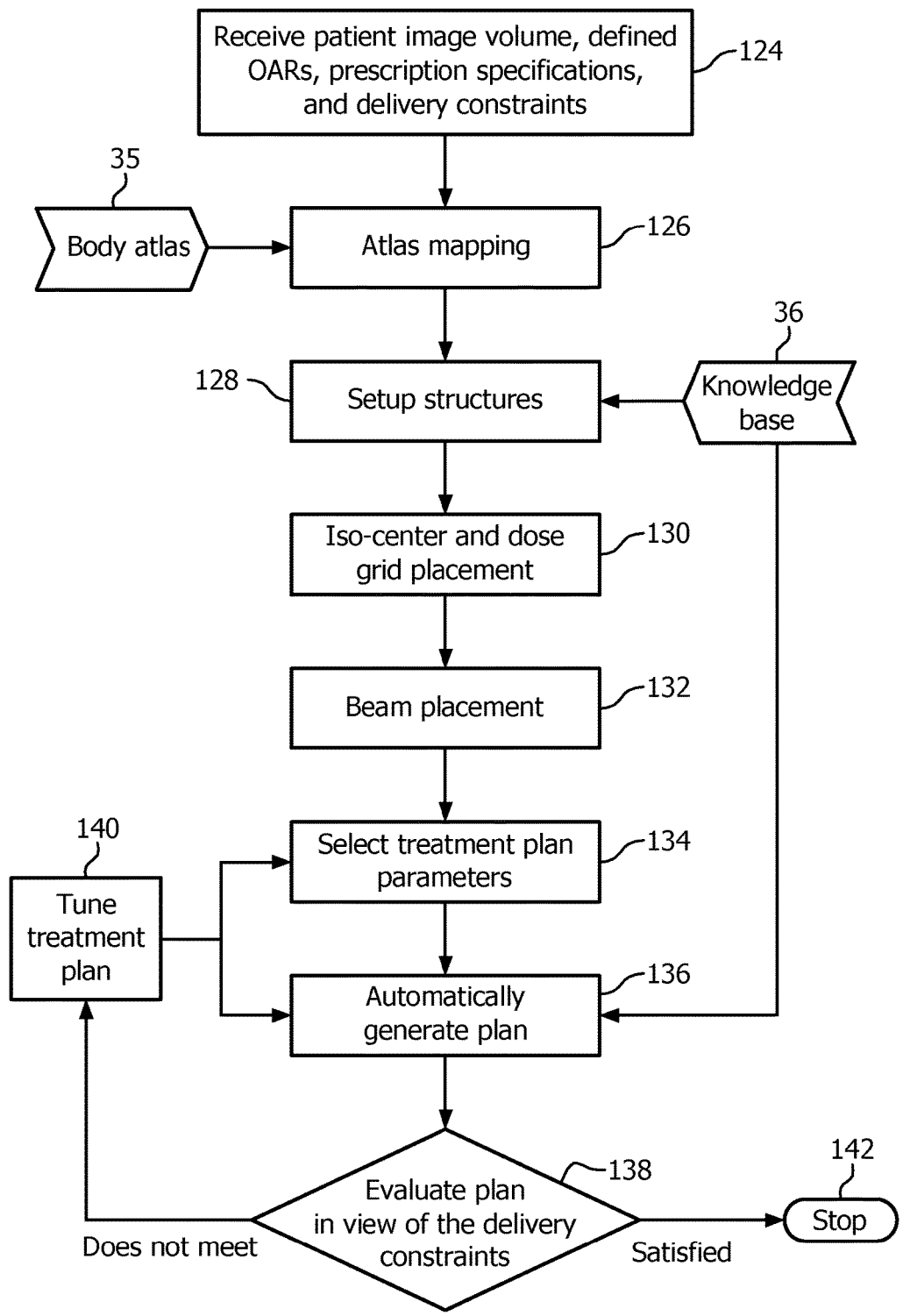
FIG. 2 depicts a method to fully automate therapy planning.

FIG. 2 depicts a method for automating ROI and OAR definitions for radiation therapy treatment plan generation which can be implemented using one or more processors. At a step 124, an image volume of a patient is received such as from the scanner 16. Further, a user defines ROIs or OARs within the patient volume through the user input device 32. The user needs to only draw or define the region of interest pertaining to the desired target volume such as a tumor. The user, e.g. radiation oncologist or technician, prescribes plan specifications and therapy delivery constraints.

At a step 126, locations of OARs in the ROIs are mapped to the body atlas 35. The atlas mapping allows rigid and deformable image registration based mapping of input OARs to the structures in the body atlas 35. The atlas mapping step also uses nomenclature anatomical site relations of the input OARs.

At a step 128, structures within the ROIs of the image volume are determined and set up using the knowledgebase 36. Structures are created considering knowledgebase parameters such as avoidance margins in clinical practice, auto-planning specific residual and difference structures.

At a step 130, iso-center and dose grid placement is performed. The iso-center plane is determined considering cavity and homogeneity constraints. The dose grid is placed such that it covers all input OARs and targets within the ROIs.

At a step 132, the beams are placed according to optimal beam angles. The optimal beam angles are determined in accordance with anatomy and patient geometry restrictions. At a step 134, treatment plan parameters are selected based on delivery constraints and machine specific capabilities. At a step 136, the treatment plan is automatically generated using the dose objectives based on clinical goals and priorities from the knowledgebase 36. Tuning and formulation of dose objectives are done automatically to generate an optimal treatment plan.

At a step 138, the generated treatment plan is evaluated against user defined dose and plan delivery constraints. If the delivery constraints are not met, the automatically generated treatment plan is tuned, at a step 140, according to a reevaluation of beam placements and treatment plan parameters. If the delivery constraints are satisfied, the method is complete 142.

It is appreciated that a user may exercise increased control of the automatic plan generation by confirming automatically determined selections after some or all of the steps. It is further appreciated that a user may tweak the knowledgebase 36 templates based on generated plans or other experience.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field programmable gate array (FPGA), and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a liquid crystal display (LCD), a light emitting diode (LED) display, a plasma display, a projection display, a touch screen display, and the like.

Although the system and method of the present disclosure have been described with reference to exemplary embodiments thereof, the present disclosure is not limited to such exemplary embodiments. Rather, the system and method disclosed herein are susceptible to a variety of modifications, enhancements and/or variations, without departing from the spirit or scope hereof. Accordingly, the present disclosure embodies and encompasses such modifications, enhancements and/or variations within the scope of the claims appended hereto.

The invention claimed is:

1. An automated treatment planning system comprising:
a planning image memory configured to store a volume diagnostic image;
a user interface device configured for a user to input data defining a plurality of regions of interest within the volume diagnostic image;
a ROI mapper having a processor configured to:
receive the volume diagnostic image and the plurality of regions of interest defined within the volume diagnostic image;
map the plurality of regions of interest within the volume diagnostic image to a body atlas to determine corresponding anatomical locations within the plurality of regions of interest; and
map each region of interest of the plurality of regions of interest to the body atlas to select correct corresponding anatomical structures by calculating a similarity metric score between each region of interest of the plurality of regions of interest and each anatomical structure of the body atlas; and
a planning module configured to generate a treatment plan using the mapped plurality of regions of interest.

2. The system according to claim 1, wherein the ROI mapper is further configured to:
associate the anatomical structure of the body atlas having a highest similarity metric score with an individual region of interest.

3. The system according to claim 1, wherein the planning module is further configured to:
receive a treatment plan template based upon the mapped regions of interests from a knowledgebase; and
generate an optimal treatment plan according to the treatment plan template.

4. The system according to claim 3, wherein the treatment plan template includes automated clinical goals and priorities that are unique to the anatomical structures mapped to the plurality of regions of interest.

5. The system according to claim 1, wherein the user interface device is configured to receive dose and plan requirements from a user.

6. The system according to claim 5, wherein the planning module is further configured to:
determine whether the generated plan meets user input requirements; and
in response to the generated plan failing to satisfy the user input requirements, iteratively tune dose and plan constraints such that the user input requirements are satisfied.

7. A method of automating treatment planning, comprising:
receiving a volume anatomical image of a patient including a plurality of user-defined regions of interest indicated within the image volume;
mapping of the plurality of regions of interest to a body atlas to determine anatomical locations within the plurality of regions of interest; and
mapping each region of interest of the plurality of regions of interest to the body atlas to select correct corresponding anatomical structures includes including;
calculating a similarity metric score between each region of interest of the plurality of regions of interest and each anatomical structure of the body atlas; and generating a treatment plan using the mapped plurality of regions of interest.

8. The method according to claim 7, further including:
when a highest similarity metric score exceeds a threshold metric score associating the anatomical structure of the body atlas having a highest similarity metric score with an individual one of the plurality of regions of interest.

9. The method according to claim 7, wherein the generating step includes:
receiving a treatment plan template based upon the mapped regions of interests from a knowledgebase; and
generating the treatment plan according to the treatment plan template.

10. The method according to claim 9, wherein the treatment plan template includes automated clinical goals and priorities that are unique to the anatomical structure mapped to the plurality of regions of interest.

11. The method according to claim 7, further including:
initially receiving dose and plan requirements from a user via a user input.

12. The method according to claim 11, wherein the treatment plan generating step further includes:
determining whether the generated treatment plan satisfies the dose and plan requirements; and
in response to the dose and plan requirements not being satisfied, iteratively tuning dose and plan constraints until the dose and plan requirements are satisfied.

13. A non-transitory computer readable medium carrying software for controlling one or more processors to perform the method of claim 7.

14. An automated treatment planning system comprising:
a planning image memory which stores a volume diagnostic image;
a user interface device configured for a user to input data defining a plurality of regions of interest within the volume diagnostic image; and
one or more processors configured to:
receive the volume diagnostic image and the plurality of regions of interest indicated within the volume diagnostic image;
map the plurality of regions of interest of the volume diagnostic image to anatomical structures using a body atlas;
rank anatomical structures in the body atlas according to a similarity score to a particular region of interest;
select a one of the anatomical structures ranked with a highest similarity score;
access a template associated with the selected one of the anatomical structures to receive dose and plan requirements; and
generate a treatment plan using the template requirements.

15. The automated treatment planning system according to claim 14, wherein the one or more processors are further configured to:
determine whether the generated treatment plan meets user input requirements; and
in response to the user input requirements not being met, iteratively tune dose and plan constraints such that the user input requirements are satisfied.

* * * * *